United States Patent
Moon et al.

(10) Patent No.: US 9,103,768 B2
(45) Date of Patent: Aug. 11, 2015

(54) ANALYSIS SYSTEM AND METHOD FOR VISUALIZING HEAT CONDUCTION

(71) Applicant: Hyundai Motor Company, Seoul (KR)

(72) Inventors: You Sung Moon, Gyeonggi-do (KR); Jin Woo Kwak, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 221 days.

(21) Appl. No.: 13/680,654

(22) Filed: Nov. 19, 2012

(65) Prior Publication Data

US 2013/0223474 A1    Aug. 29, 2013

(30) Foreign Application Priority Data

Feb. 29, 2012    (KR) .................. 10-2012-0021509

(51) Int. Cl.
  *G01N 25/18*    (2006.01)
  *G01J 5/00*    (2006.01)

(52) U.S. Cl.
  CPC ..................... *G01N 25/18* (2013.01)

(58) Field of Classification Search
  USPC .................. 374/124, 44, 141, 121
  See application file for complete search history.

(56) References Cited

U.S. PATENT DOCUMENTS

| | | | |
|---|---|---|---|
| 5,653,539 A * | 8/1997 | Rosengaus ............... 374/159 |
| 6,585,408 B2 * | 7/2003 | El-Gabry et al. ........... 374/43 |
| 7,422,365 B2 * | 9/2008 | Chamberlain et al. ...... 374/120 |
| 8,186,873 B1 * | 5/2012 | Madding .................. 374/43 |
| 2004/0028113 A1 * | 2/2004 | Schlagheck et al. ......... 374/57 |
| 2005/0002435 A1 * | 1/2005 | Hashimoto et al. .......... 374/43 |
| 2005/0147150 A1 * | 7/2005 | Wickersham et al. ....... 374/120 |
| 2006/0114965 A1 * | 6/2006 | Murphy et al. ............. 374/120 |
| 2007/0036199 A1 * | 2/2007 | Ouyang et al. ............. 374/120 |
| 2009/0016402 A1 * | 1/2009 | Bunker et al. ............. 374/43 |
| 2009/0201971 A1 * | 8/2009 | Goldammer et al. ......... 374/45 |
| 2010/0046574 A1 * | 2/2010 | Hamann et al. ............ 374/43 |
| 2011/0278113 A1 * | 11/2011 | Nishimura et al. ......... 188/106 P |
| 2011/0278455 A1 * | 11/2011 | Choi et al. ............... 250/330 |

FOREIGN PATENT DOCUMENTS

| | | | |
|---|---|---|---|
| JP | 03186748 A | * | 8/1991 |
| JP | 2004325141 A | | 11/2004 |
| JP | 2007064917 A | | 3/2007 |
| JP | 2008051744 A | | 3/2008 |
| JP | 2011069652 A | | 4/2011 |
| KR | 10-1067901 | | 7/2004 |
| KR | 10-2011-0090209 | | 8/2011 |

* cited by examiner

*Primary Examiner* — Mirellys Jagan
(74) *Attorney, Agent, or Firm* — Mintz Levin Cohn Ferris Glovsky and Popeo, P.C.; Peter F. Corless

(57) ABSTRACT

Disclosed is an analysis system and method for visualizing heat conduction of a solid state sample. The analysis system includes a sealed jig chamber, a jig, an air tempering unit, and a thermal image camera. The sealed jig chamber includes a chamber door for opening/closing the jig chamber. The jig is removeably mounted in the jig chamber and comprises a heat source in surface contact with a solid state sample to induce the heat conduction of the solid state sample. The air tempering unit supplies hot air into the jig and supplies cool air into the jig chamber. The thermal image camera photographs the heat conduction of the solid state sample to acquire a thermal image or video.

10 Claims, 10 Drawing Sheets

< SECTION A-A >

< SECTION B-B >

ANALYSIS SYSTEM AND METHOD FOR VISUALIZING HEAT CONDUCTION

CROSS-REFERENCE TO RELATED APPLICATION

This application claims under 35 U.S.C. §119(a) the benefit of Korean Patent Application No. 10-2012-0021509 filed Feb. 29, 2012, the entire contents of which are incorporated herein by reference.

BACKGROUND (a) Technical Field

The present invention relates to an analysis system and method for visualizing heat conduction. More particularly, the present invention relates to an analysis system and method for visualizing heat conduction that clearly acquires the heat conduction characteristics of various kinds of solid state samples.

(b) Background Art

Recently, thermal conductivities that are bibliographically reported by thermal conductivity measurement standardization methods for quantitative digitization of heat conduction of a solid state sample are distinguished according to the measurement methods and the types of samples used. Due to the absence of a standardized system for thermographic imaging for visualization heat conduction in actual samples, there are many variables that influence the results such as ambient environments including temperature, convection and humidity, interfacial resistance between a sample and a heat source, sample size, and non-uniform heat transfer from the heat source to the sample during the visualization analysis of heat conduction. Accordingly, the conventional techniques for analyzing heat conduction of a sold state sample are severely limited.

Currently, the standard tests related to heat conduction measurement measure the thermal conductivity of the solid state sample and provide a quantitative analysis. However, due to various heat conduction measurement methods, values vary even from one sample to another even when the samples are exactly the same when the conventional measurement methods are utilized. Also, in case of a composite sample, the thermal conductivities in the thickness direction and longitudinal direction (or surface direction) of two identical samples typically differ according to their filler orientations and dispersion degrees of the sample.

Most thermal conductivity measurement methods are optimized for the thermal conductivity measurement in the thickness direction. The thermal conductivity in the longitudinal direction, however, is often greatly different form the thermal conductivity in the thickness direction due to the shape of a sample holder for testing the sample in the longitudinal direction (or planar direction). The shape of the hold is also manufactured differently than the type of holder used for testing the thermal conductivity of a solid state sample. Thus the conventional methods are not entirely reliable.

Generally, heat conduction in a solid state sample occurs in an environment in which a temperature gradient exists, and thermal energy from a high temperature location is transferred in a form of phonon through the crystal lattice of the sample. When a thermal image camera is used, the thermal diffusion of the sample is detected by the range (pixel) temperature variation to be displayed on a display with a certain degree of color contrast.

However, as described above, due to the absence of a standardized system for visualizing the heat conduction in an actual sample, the phenomenon analysis is being limited due to influences from many different variables such as ambient environments including temperature, convection and humidity, interfacial resistance between a sample and a heat source, sample size, and non-uniform heat transfer from the heat source to the sample during the visualization analysis.

Particularly, in case of a polymer composite sample, the filler orientation and dispersion vary according to its manufacturing methods. Generally, in a sample manufactured by injection molding, a filler receives a delivery force to be oriented in the injection (longitudinal) direction, and thus the filler forms a heat transfer path in the injection direction, leading to the heat conduction characteristics higher than those in the thickness direction. This shows a difference in degree according to the injection conditions, the crystallinity of polymer resin, the size and shape of the filler, and the surface characteristics of the filler. Accordingly, a clearer analysis of the heat conduction characteristics in the longitudinal direction and thickness direction of a sold state sample is needed.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention provides a standardized analysis system and method for visualizing heat conduction, which can measure the heat conduction characteristics of a solid state sample in a thickness direction, longitudinal direction, and radial direction to visualize the thermal diffusion according to the thermal transfer directivity in consideration of the crystal lattice, i.e., thermal isotropy due to the atomic orientation and array structure, of the solid state sample having various heat conduction characteristics, in verifying the thermal diffusion speed and investigating the heat conduction characteristics according to the types of samples through visualization of the heat conduction of the solid state sample.

The present invention also provides a standardized analysis system and method for visualizing heat conduction, which can measure the heat conduction characteristics in the thickness direction, longitudinal direction, and radial direction, by visualizing the heat radiation due to convection varying according to the thermal conductivity of a solid state sample.

In one aspect, the present invention provides an analysis system for visualizing heat conduction, including: a sealed jig chamber including a chamber door part for opening/closing the jig chamber; a jig removeably mounted in the jig chamber and including a heat source in surface contact with a solid state sample to induce the heat conduction of the solid state sample; an air tempering unit configured to supply hot air into the jig or supplying cool air into the jig chamber and a thermal image camera photographing the heat conduction of the solid state sample to acquire a thermal image or video.

In an exemplary embodiment, the jig may include at least one of a jig configured to measure the heat conduction in a thickness direction of the solid state sample, a jig configured to measure the heat conduction in a longitudinal direction of the solid state sample, and a jig configured to measure the heat conduction in a radial direction of the solid state sample.

In another exemplary embodiment, the jig configured to measure the heat conduction in the thickness direction may include a planar type heat source that may be disposed on one surface of the jig and is in complete surface contact with one surface of the solid state sample, and a hot air inlet and a hot air outlet configured to receive and discharge hot air to increase the temperature of the planar type heat source.

In still another exemplary embodiment, the jig configured to measure the heat conduction in the longitudinal direction may include a circular type heat source that may be disposed on one surface of the jig and is in surface contact with a center of one surface of the solid state sample, and a hot air inlet and a hot air outlet configured to receive and discharge hot air to increase the temperature of the circular type heat source.

In yet another exemplary embodiment, the jig for measuring the heat conduction in the radial direction may include a pocket type heat source that may be completely in contact with the surface of one end portion of the solid state sample, and a hot air inlet and a hot air outlet that are disposed at the opposite side of the heat source and receive and discharge hot air for increasing a temperature of the heat source.

In still yet another exemplary embodiment, the air tempering unit may include a hot air unit for generating and supplying hot air for uniformly increasing a temperature of the heat source of the jig, a cool air unit for generating and supplying cool air that flows into the jig chamber to cool the solid state sample, and a control unit for controlling a temperature of the hot air and the cool air.

In a further exemplary embodiment, the air tempering unit may be connected to hot air ducts that connect a hot air outlet and a hot air inlet of the air tempering unit to a hot air inlet and a hot air outlet of the jig, respectively, and may be connected to a cool air duct that connects a cool air outlet of the air tempering unit to a cool air inlet of the jig chamber.

In another further exemplary embodiment, the jig may be formed of a heat-insulating material except the heat source formed of an aluminum material.

In another aspect, the present invention provides an analysis method for visualizing heat conduction, including: preparing a sealed jig chamber connected to an air tempering unit for generating and supplying hot air and cool air through a duct; selecting and installing a jig appropriate for heat conduction measurement of a solid state sample in the jig chamber; inducing the heat conduction by heating a heat source of the jig using the air tempering unit and transferring heat to the solid state sample mounted in the jig through the heat source; photographing the solid state sample using a thermal image camera to acquire a thermal image or a thermal diffusion video; and analyzing heat conduction characteristics of the solid state sample using the thermal image or the thermal diffusion video.

In an exemplary embodiment, the inducing of the heat conduction may include at least one of: inducing the heat conduction in a thickness direction of a planar sample by allowing one surface of the planar sample to be completely in surface contact with a planar type heat source; inducing the heat conduction in a longitudinal direction of the planar sample by inserting only one end portion of the planar sample into a pocket type heat source to be in surface contact with the pocket type heat source while being surrounded by the pocket type heat source; and inducing the heat conduction in a radial direction by allowing the planar sample to be in surface contact with a circular type of heat source at a center of one surface thereof.

In another exemplary embodiment, the analysis method may include: cooling the solid state sample mounted in the jig through convection by supplying cool air into the jig chamber through the air tempering unit; photographing the solid state sample using a thermal image camera to acquire a thermal image or a thermal diffusion video according to cooling of the solid state sample; and analyzing heat conduction characteristics according to heat radiation of the sample using the thermal image or the thermal diffusion video.

Other aspects and exemplary embodiments of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
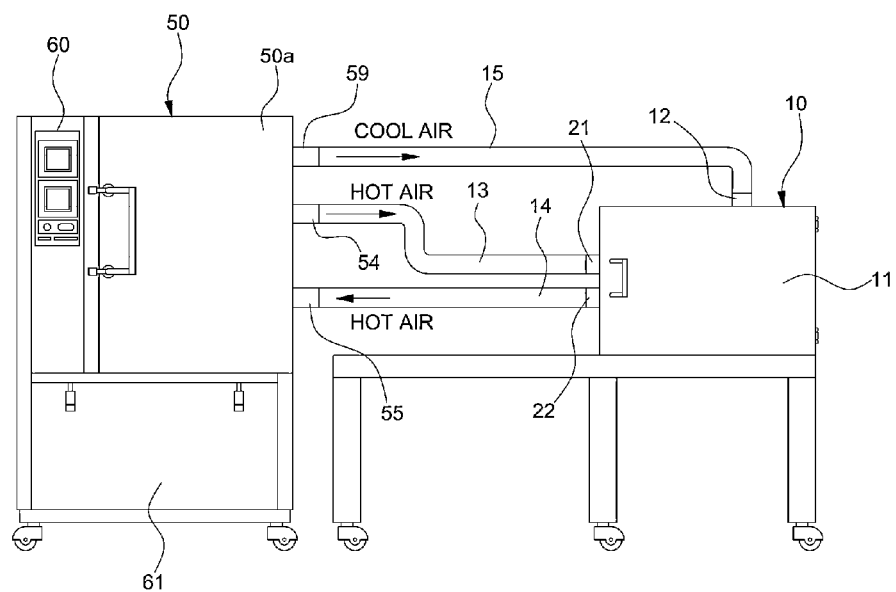
FIG. 1 is a view illustrating an analysis system for visualizing heat conduction according to an exemplary embodiment of the present invention.

Reference numerals set forth in the Drawings includes reference to the following elements as further discussed below:

10: jig chamber
11: chamber door part
12: cool air inlet
13, 14: hot air duct
15: cool air duct
20: jig for measuring heat conduction in thickness direction
21: hot air inlet
22: hot air outlet
23: heat source
24: sample holder
30: jig for measuring heat conduction in longitudinal direction
31: hot air inlet
32: hot air outlet
33: heat source
40: jig for measuring heat conduction in radial direction
41: hot air inlet
42: hot air outlet 43: heat source
44: sample holder
50: air tempering unit
50a: door part
51: hot air unit
52: heating coil
53: hot air blower
54: hot air outlet
55: air inlet
56: cool air unit
57: cooling coil
58: cool air blower
59: cool air outlet
60: control unit
61: storage space
70: thermal image camera It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The above and other features of the invention are discussed infra.

The present invention relates to an analysis system and method for visualizing heat conduction, which can perform analysis of heat conduction characteristics according to the types of samples provided by measuring (or photographing) and analyzing thermal diffusion in the thickness direction, longitudinal direction, and three-dimensional radiation direction of a solid state sample in consideration of thermal isotropy of the solid state sample.

Thus, the present invention provides a standardized system and method for accurately analyzing heat conduction characteristics according to the types of samples provided by measuring and analyzing a thermal diffusion process occurring in a solid state sample using a thermal image.

Hereinafter, exemplary embodiments of the present invention will be described in detail with reference to the accompanying drawings. Also, the term "longitudinal direction" of a sample may include a two-dimensional plane direction perpendicular to a thickness direction.

Typically, all solid state substances may perform a lattice vibration at a temperature higher than absolute zero. In this case, thermal diffusion can be visualized by a thermal image camera that detects infrared rays having thermal characteristics among electromagnetic waves emitted when atoms and/or molecules vibrate.

In an embodiment of the present invention, when heat conduction of a solid state sample is visualized using a thermal image camera, a jig that can measure thermal conductivity in the thickness direction, longitudinal direction, and radial direction of the sample may be used to visualize thermal diffusion according to thermal transfer directional properties of the sample in consideration of thermal anisotropy of various solid state samples.

For example, in case of a composite sample, since there are differences in the heat conduction characteristics of the thickness direction and the longitudinal direction according to the injection conditions, crystallinity of polymer resin, size and shape of filler, and surface characteristics of filler, accurate and clear analysis of the heat conduction characteristics in the longitudinal direction and thickness direction of the sample may be needed.

Figure 4:
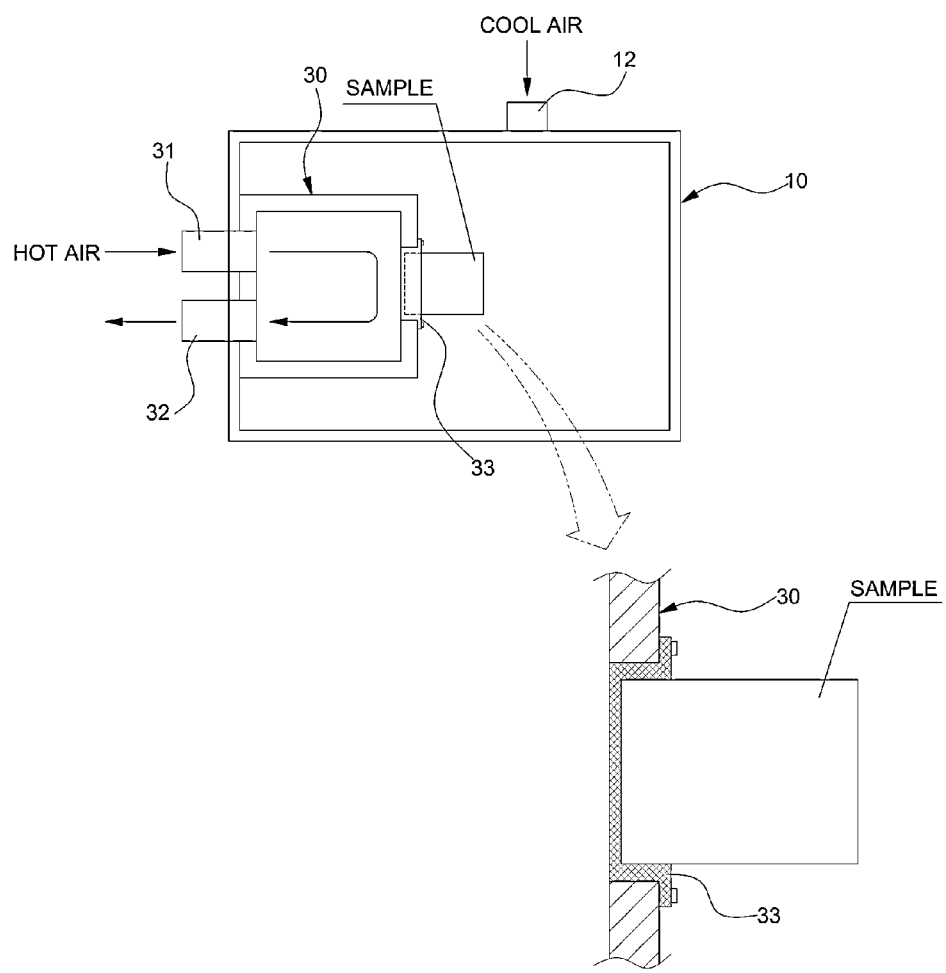
FIG. 4 is a view illustrating a jig for measuring heat conduction in a longitudinal direction according to an exemplary embodiment of the present invention.
Figure 5A:
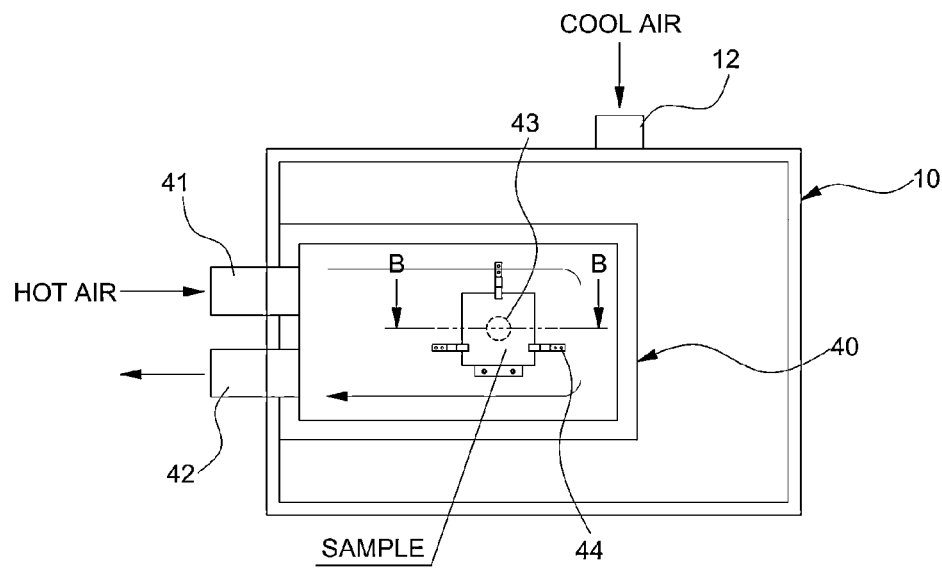
FIG. 5A-B is a view illustrating a jig for measuring heat conduction in a radial direction according to an exemplary embodiment of the present invention.
Figure 5B:
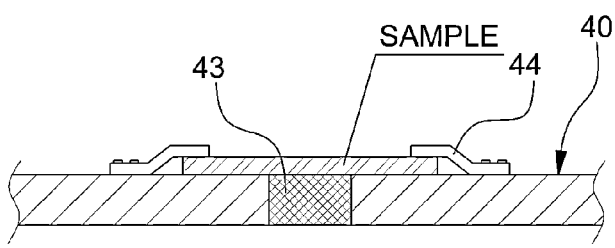

The jig may include three types of jigs, for example, a jig 20 configured to measure heat conduction in a thickness direction (See FIG. 3A-B), a jig 30 configured to measure heat conduction in a longitudinal direction (See FIG. 4), and a jig 40 configured to measure heat conduction in a radial direction (See FIG. 5A-B).

1. Jig for Measuring Heat Conduction in Thickness Direction (20)

Figure 3A:
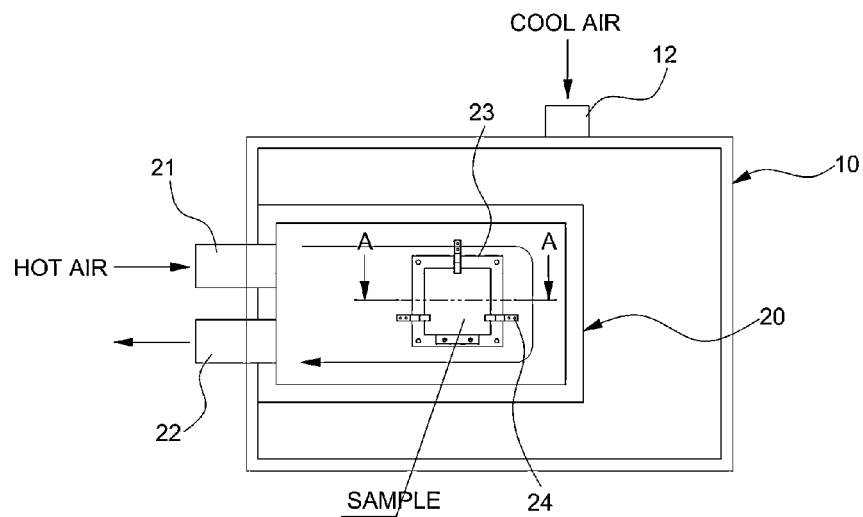
FIG. 3A-B is a view illustrating a jig for measuring heat conduction in a thickness direction according to an exemplary embodiment of the present invention.
Figure 3B:
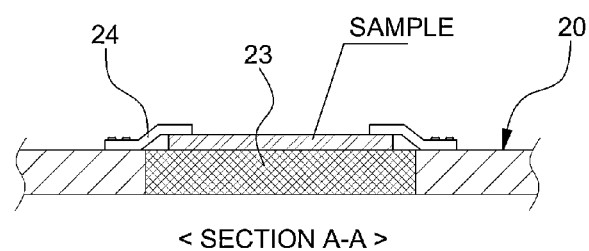

As shown in FIG. 3A-B, the jig 20 for measuring heat conduction in a thickness direction may include a hot air inlet 21 configured to receive hot air passing through the jig 20 and a hot air outlet 22 configured to discharge hot air passing through the jig 20 at one side thereof, and may be formed to have a rectangular shape. The jig 20 may further include a heat source 23 on the upper side thereof. The heat source 23 may be heated by hot air circulating in the jig 20 through the hot air inlet 21 and the hot air inlet 22.

As shown in FIG. 3B, which is a cross sectional view of the cut along lines A-A of FIG. 3A, the heat source 23 may be formed to have a size and shape (e.g., planar shape) such that the heat source 23 can be completely in contact with one surface (e.g., surface perpendicular to the thickness direction) of a solid state sample. Also, a sample holder 24 may be disposed around the heat source 23 on the upper surface of the jig 20 to secure a solid state sample.

As stated above, the jig 20 for measuring heat conduction in the thickness direction may be in contact with one entire surface (surface perpendicular to the thickness direction) of a solid state sample. Thermal energy emitted from the heat source 23 may be delivered to the entire surface of the solid state sample perpendicular to the thickness direction, and thermal energy delivered to the surface of the solid state sample may be diffused in the thickness direction of the sample to be discharged from the other surface (opposite surface) of the sample. In this case, the other surface of the solid state sample may be photographed by a thermal image camera 70 to acquire a thermal image for analysis of heat conduction.

2. Jig for Measuring Heat Conduction in Longitudinal Direction (30)

As shown in FIG. 4, the jig 30 for measuring heat conduction in a longitudinal direction may include a hot air inlet 31 configured to receive hot air passing through the jig 30 and a hot air outlet 32 configured to discharge hot air passing through the jig 30 on one side thereof, and may be formed to have a rectangular shape. The jig 30 may further include a heat source 23 at the opposite side thereof. The heat source 33 may be heated by hot air circulating in the jig 30.

The heat source 33 may be embodied as a pocket type heat source in which, e.g., one third of the solid state sample is inserted into a pocket in the heat source 33 in the lengthwise direction as shown in FIG. 4. Accordingly, the heat source 33 is in surface contact with the portion of the sample surrounding the one third of the solid state sample inserted into the pocket type heat source and may be heated via hot air passing through the jig 30, and thus thermal energy may be delivered to the solid state sampled accordingly.

As mentioned above about one third of one end of the solid state sample mounted in the jig 30 for measuring heat conduction in the longitudinal direction may be surrounded by the heat source 33 to be in surface contact with the heat source 33, and thus thermal energy emitted from the heat source 33 may be delivered to the sample and diffused in the longitudinal direction of the sample to be discharged from the other end portion of the sample. In this case, the other end portion (portion protruding out of the jig 30) of the solid state sample may be photographed by the thermal image camera 70 to acquire a thermal image for analysis of heat conduction.

3. Jig for Measuring Heat Conduction in Radial Direction (40)

As shown in FIGS. 5A-B, the jig 40 for measuring heat conduction in a radial direction may include a hot air inlet 41 configured to receive hot air passing through the jig 40 and a hot air outlet 42 configured to discharge hot air passing through the jig 40 on one side thereof, and may be formed to have a rectangular shape. The jig 40 may further include a heat source 43 on the upper side thereof. The heat source 43 may be heated by hot air circulating in the jig 40 through the hot air inlet 41 and the hot air inlet 42.

As stated above, the heat source 43 may be formed to have a circular shape such that the heat source 43 can be partially in surface contact with one surface (surface perpendicular to the thickness direction) of a solid state sample and disposed at a central portion of one surface of the solid state sample instead of being entirely in surface contact with one surface of the solid state sample. Also, a sample holder 44 may be disposed around the heat source 43 on the upper surface of the jig 40 to secure a solid state sample.

The jig 40 may measure heat conduction that is diffused in the radial direction of three-dimension to measure the heat conduction characteristics in which thermal diffusion occurs in the thickness and longitudinal directions. The heat source 43 may deliver thermal energy in a point source form instead of the entire area of the sample. Heat primarily delivered in the thickness direction may be radially diffused to be discharged out of the other surface (opposite side of one surface in surface contact with the heat source) of the solid state sample. In this case, the other surface of the solid state sample may be photographed by the thermal image camera 70 to acquire a thermal image for analysis of heat conduction.

Hot air flowing into the jigs 20 and 40 for measuring heat conduction in the thickness and radial directions may be discharged after circulating around the heat sources 23 and 43 of the jigs 20 and 40, and hot air flowing into the jig 30 for measuring heat conduction in the longitudinal direction may be discharged after directly contacting the heat source 33 of the jig 30. In these processes, the heat sources 23, 33 and 43 may be heated.

Although not shown, the jigs 20, 30 and 40 may have passages for guiding hot air to the heat sources 23, 33 and 43, and the passages may be defined by partitions. Hot air flowing into the jigs 20, 30 and 40 may be smoothly circulated by the partitions and may be intensively supplied to the heat sources 23, 33 and 43. In case of the jig 30 for measuring heat conduction in the longitudinal direction, since the heat source 33 is inserted into the jig 30, hot air flowing into the jig 30 may directly contact the heat source 33 due to the structure of the partitions.

Also, the sample holders 24 and 44 of the jig 20 and 40 may be configured not to interfere with photographing of the thermal image camera 70. Thus, the frontal visual field of the thermal image camera 70 may be clear of unwanted objects, and interference with the heat conduction analysis may be minimized. Also, a contact area with the solid state sample may be minimized to prevent heat loss.

The jigs 20, 30 and 40 may be configured such that contact surfaces between the solid state sample and the heat sources 23, 33 and 43 are maximized under each condition to shorten temperature-rising time and improve the thermal diffusion of the sample.

The jigs 20, 30 and 40 may be formed of a heat-insulating material at portions other than the heat sources 23, 33 and 43 formed of a metallic material to minimize heat loss at the portions other than the heat sources 23, 33 and 43. For example, the heat sources 23, 33 and 43 may be formed of an aluminum material with high thermal conductivity, and may have a minimum thickness to increase heat supply efficiency and minimize interference during photographing of the thermal image camera 70.

Although varying in shape of the jigs 20, 30 and 40, the sample may be mounted to be in surface contact with the heat sources 23, 33 and 43. In order to minimize the interfacial resistance reducing the thermal transfer efficiency between the sample and the heat sources 23, 33 and 43 of the jigs 20, 30 and 40, the surfaces of the heat sources 23, 33 and 43 of the jigs 20, 30 and 40 may be cleaned using ethanol, and then may be coated with thermal compound (thermal paste) with thermal conductivity of about 10 W/mK or more to minimize gaps between the sample and the heat sources 23, 33 and 43.

Also, since the visualization result varies according to a thermal diffusion distance in the solid state sample, it is necessary to standardize the sample to be measured. For example, the dimensions of the sample may be standardized to 100 mm in length, 100 mm in width, and 3 mm in thickness to analyze the heat conduction characteristics.

In order to allow (or form) a uniform temperature with respect to all surfaces of the solid state sample contacting the heat sources 23, 33 and 43, an air tempering unit 50 may be used to circulate hot air for heating the heat sources 23, 33 and 43 to a uniform temperature instead of heating the sample via conventional heating wires or resistors.

Figure 2:
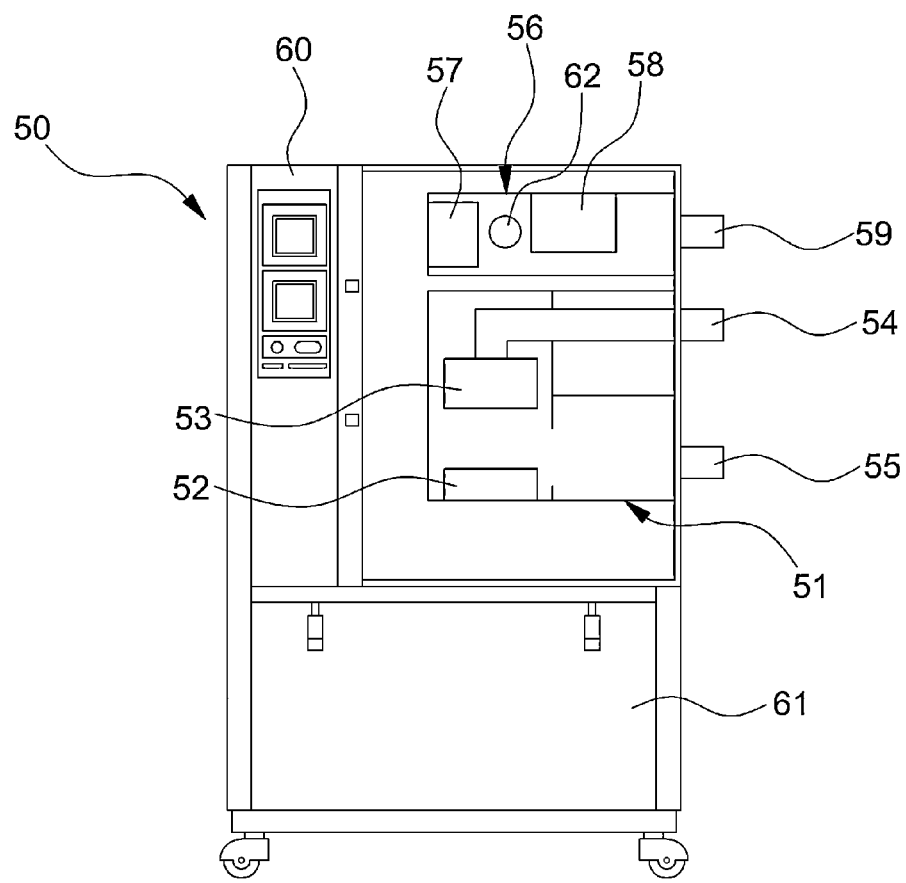
FIG. 2 is a view illustrating an air tempering unit of an analysis system for visualizing heat conduction according to an exemplary embodiment of the present invention.

The air tempering unit 50 may control the temperature of the heat sources 23, 33 and 43 using hot air. As shown in FIG. 2, the air tempering unit 50 may include a hot air unit 51 for generating and supplying hot air, a cool air unit 56 for generating and supplying cool air, and a control unit 60 for controlling the temperature of hot air and cool air.

The hot air unit 51 may include a heating coil (or resistor) 52 and a hot air blower 53. The heating coil 52 may radiate heat using electric resistance, and the maximum radiation temperature may be determined by the number of wound coils. The hot air blower 53 may send internal air heated by the heating coil 52 to a desired place, i.e., the hot air outlet 54 of the air tempering unit 50 through a passage tube (not shown).

The hot air unit 51 may supply hot air with a maximum temperature of about 250° C., and may increase the thermal efficiency by an air circulation method. Hot air discharged from the hot air outlet 54 may be supplied into the hot air inlets 21, 31 and 41 of the jigs 20, 30 and 40.

The cool air unit 56 may include a cooling coil (or resistor) 57 and a cool air blower 53. The cooling coil 57 may radiate heat using electric resistance, and the maximum radiation temperature may be determined by the number of wound coils. The cool air blower 53 may send internal air cooled by heat transference the cooling coil 57 to a desired place, i.e., the cool air outlet 59 of the air tempering unit 50 through a passage tube/duct (not shown).

Furthermore, the cool air unit 56 may include an air intake duct 62 that is positioned to receive external air at one side thereof as shown in FIG. 2. The cool air unit 56 may supply cool air with a maximum temperature of about 50° C., and the wind velocity may be controlled by the rotational velocity of the cool air blower 53. Cool air discharged from the cool air outlet 59 may be supplied into the cool air inlet 12 of the jig chamber 10. Air from the air intake duct 55 is illustrated as supplying the hot air to the hot air unit 51.

The control unit 60 may be provided to set details of the air tempering unit 50. The control unit 60 may include a cool air temperature controlling unit, a cool air velocity controlling unit, and a cool air direction controlling unit. The cool air temperature controlling unit may control the temperature of cool air to a certain temperate (e.g., from room temperature to about 50° C.) using the cooling coil 57. The cool air velocity controlling unit may control the velocity of cool air to a certain velocity (e.g., from about zero to about 6 m/s) using the cool air blower 58. The cool air direction controlling unit may control the direction of cool air using a movable cool air duct 15. Thus, it is possible to analyze heat radiation of the solid state sample by convection in the jig chamber 10 using the cool air unit 56 under the same conditions as general convection conditions.

The ducts 13 to 15 may be tubes that allow hot and cool air generated in the air tempering unit 50 to flow into the jigs 20, 30 and 40 and the jig chamber 10. The ducts 13 to 15 may be configured to minimize heat loss through a finish by a heat-insulating material, e.g., glass fiber, and may be configured with a fixed type such that circulating air is not affected by external shocks.

As shown in FIG. 1, the ducts 13 to 15 may include hot air ducts 13 and 14, and a cool air duct 15. The hot air ducts 13 and 14 may connect the hot air outlet 54 and the air inlet 55 of the air tempering unit 50 for discharging and receiving hot air generated in the hot air unit 51 to the hot air inlets 21, 31 and 41 and the hot air outlets 22, 32 and 42 of the jigs 20, 30 and 40 mounted in the jig chamber 10, respectively. The cool air duct 15 may connect the cool air outlet 59 of the air tempering unit 50 to the cool air inlet 12 of the jig chamber 10.

The air tempering unit 50 may include a door 50a for opening/closing an internal space mounted with the hot air unit 51 and the cool air unit 56 to quickly reduce the temperature of internal hot air according to a given environment, and a storage space 61 at a lower portion thereof. The storage space 61 may be opened and closed to receive and store devices necessary for testing.

The jig chamber 10 connected to the air tempering unit 50 through the cooling air duct 15 may be configured with a sealed chamber to prevent the variation of the thermal transfer characteristics of the solid state sample due to external convection, and may include a jig mounting part (not shown) for placing and installing the jigs 20, 30 and 40 therein. The external wall of the jig chamber 10 may be heat-insulated, as well, to minimize the influence of external environments The jig chamber 10 may include a chamber door part 11 on the front side thereof and a sensor (not shown). The chamber door part 11 may be opened and closed to photograph the solid state sample using the thermal image camera 70. The sensor may measure the surface temperature of the heat sources 23, 33 and 43 of the jigs 20, 30 and 40. The measured temperature may be displayed on the control unit 60.

Figure 6:
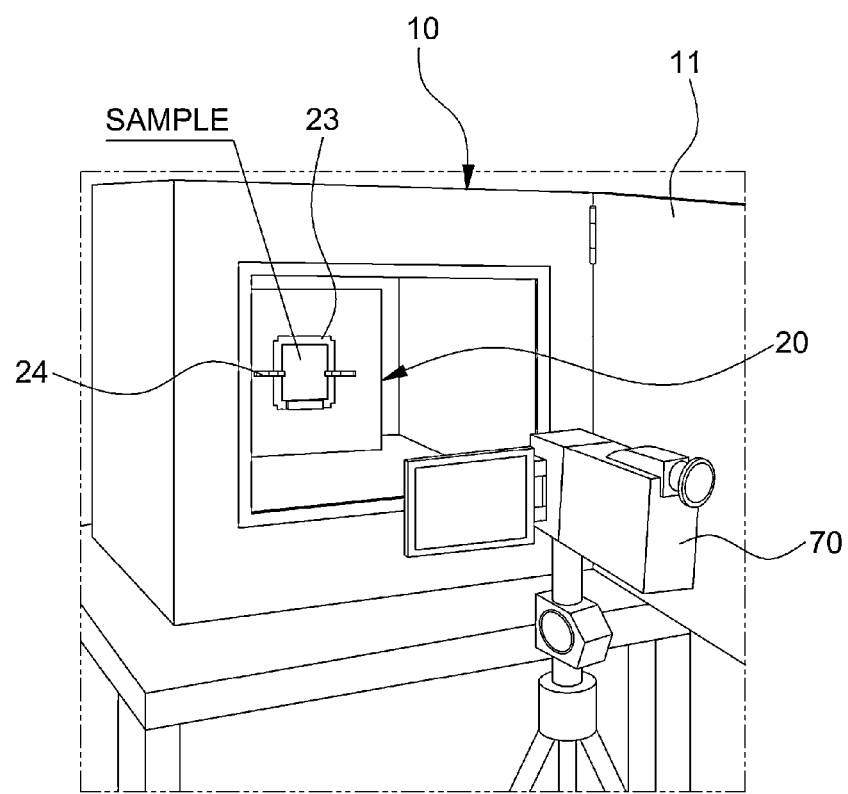
FIG. 6 is a view illustrating photographing of a heat conduction image of a solid state sample in an analysis method for visualizing heat conduction according to an exemplary embodiment of the present invention.

The thermal image camera 70 may be an apparatus for photographing the solid state sample to acquire images or videos of heat conduction. As shown in FIG. 6, the temperature of the solid state sample may be measured using an image or video acquired from the front side of the thermal image camera 70.

The heat sources 23, 33 and 43 on the surface of the jigs 20, 30 and 40 may be heated by circulating hot air that is heated by the heating coil 52 in the hot air unit 51 of the air tempering unit 50, and then flows into the hot air inlets 21, 31 and 41 by the hot air blower 53 and returns to the hot air unit 51 of the air tempering unit 50 through the hot air outlets 22, 32 and 42 of the jigs 20, 30 and 40.

In the analysis system according to the exemplary embodiment of the present invention, the jigs 20, 30 and 40 suitable for the heat conduction characteristics of the solid state sample to be measured may be mounted in the jig chamber 10, and then the solid state sample may be mounted in the jigs 20, 30 and 40. Thereafter, heat conduction of the sample may be generated by increasing the temperature of the heat sources 23, 33 and 43, and then an analysis result may be acquired using images or videos of thermal diffusion occurring in the sample and photographed by the thermal image camera 70.

The analysis system for visualizing heat conduction according to the exemplary embodiment of the present invention can perform visualization analyses of heat conduction due to temperature increase and heat radiation due to cooling (or convection).

Since the heat transfer of the solid state sample occurs by conduction, convection, and radiation, for the visualization of heat conduction due to heat radiation, internal convection conditions of the jig chamber 10 may be set in the air tempering unit 50, and a thermal image or video according to heat radiation may be measured for the visualization analysis.

The heat loss of the sample due to cooling may be obtained by analyzing measured data in consideration of three conditions such as cool air temperature, cool air velocity, and cool air direction. The heat loss may be used as data for determining the heat radiation performance in accordance with the actual situations of the sample.

All tests for analyzing the heat conduction and radiation of the solid state sample may be performed inside the jig chamber 10. Accordingly, since external influences such as convection and temperature can be excluded, reliable data can be acquired regardless of season and test site. Thus, the analysis system according to the embodiment of the present invention may be useful for standardizing heat conduction and heat radiation characteristics analysis according to the types of solid state samples.

Accordingly, the reliability of data necessary for material development can be increased by visualizing heat conduction and radiation to know substantial thermal diffusion characteristics of a material and standardizing various conditions in heat conduction measurement of the material. Also, a database of thermal conductivity of a material can be created to provide a foundation of building infrastructure and analyzing commercialization possibility for new material development.

The test examples below are provided only for illustration of the present invention, and the present invention will not be limited thereto.

TEST EXAMPLES

An exemplary test was performed to analyze heat conduction occurring when a solid state sample is heated and heat radiation occurring when the solid state sample is cooled. The application possibility of a material to a battery system module may be investigated by analyzing the heat conduction characteristics of the material according to heating and cooling.

Here, the conditions for analysis of the heat radiation were set based on the heat radiation conditions of battery system modules for electric vehicles, and a solid state sample was heated to a temperature of about 70° C. for analysis of the heat conduction due to heating 1. Heat Conduction Measurement Test of Conventional Method A hot plate 1 and a thermal image camera 2 were used as heat sources for supplying heat to a solid state sample (see FIGS. 7 and 8) utilizing the conventional method. Heat conduction was recorded according to the lapse of time to create data. The result data of the heat conduction measurement test was inversely calculated to derive the heat radiation characteristics of the sample.

a. Heat Conduction Measurement in Thickness Direction

Figure 7:
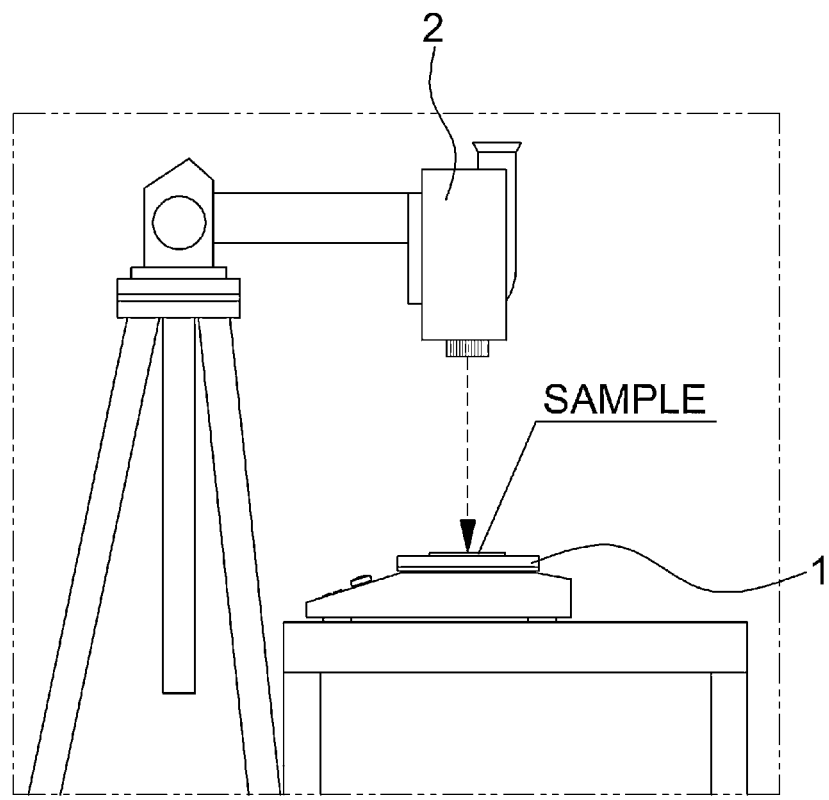
FIGS. 7 and 8 are views illustrating photographing of a heat conduction of a solid state sample in a conventional method.

A solid state sample was placed on the hot plate 1 heated to a temperature of about 70° C. to be in surface contact with the hot plate 1. As shown in FIG. 7, the solid state sample was downwardly photographed (at an interval of about 0.5 seconds) by the thermal image camera 2 including a tripod to measure the heating phenomenon of the solid state sample.

Figure 9A:
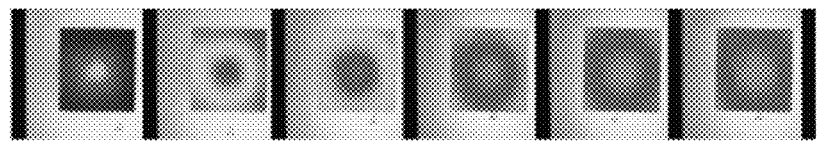
FIG. 9A-B is a view illustrating thermal images of heat conduction of two solid state samples photographed in a thickness direction according to a conventional method and arranged in order of time.
Figure 9B:
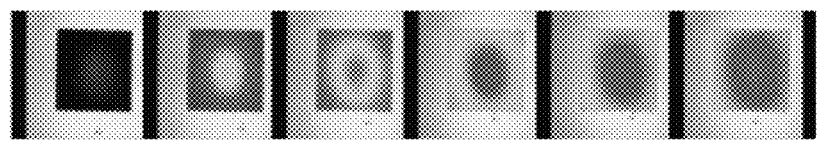

FIGS. 9A-B are views illustrating thermal images of heat conduction of two solid state samples photographed in a thickness direction and arranged in order of time.

In the thermal images of FIGS. 9A-B, it can be seen that the heat conduction of the sample occurs in the radial direction. This phenomenon means that heat of the hot plate, not the heat conduction characteristics of the sample, is not uniformly supplied to the sample. Also, since the error range of temperature to be maintained is significantly large, it can be seen that the heat conduction could not be accurately measured in the thickness direction of the sample by a typical method.

b. Heat Conduction Measurement in Longitudinal Direction

Figure 8:
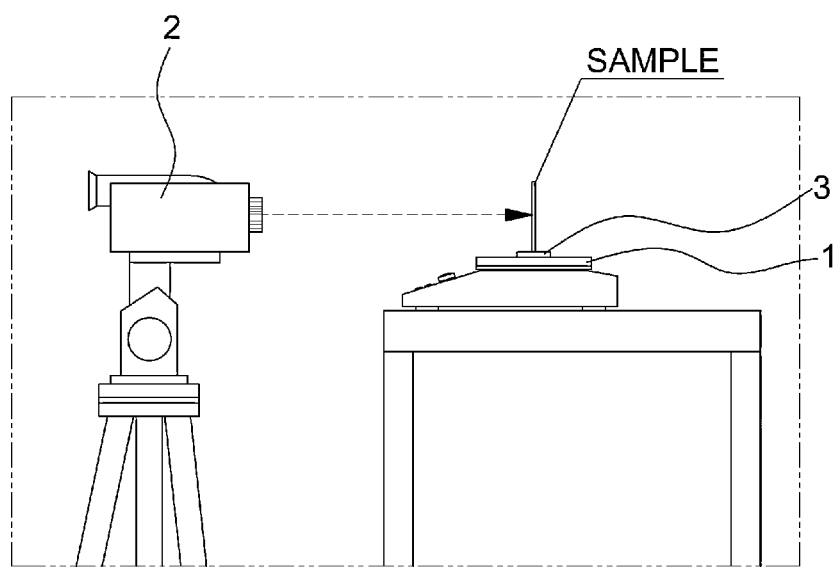

A sample support 3 having a rectangular aperture of 100 mm×2 mm×10 mm and formed of aluminum was placed on the hot plate 1 heated to a temperature of about 70° C., and then an aluminum foil was attached between the sample and the sample support 3 to insert the sample into the sample support 3 by an interference-fit method. As shown in FIG. 8, the thermal image camera 2 may be disposed on the front side of the sample that is upright in the vertical direction, and photographed the sample to measure the heat conduction of the sample.

Figure 10:
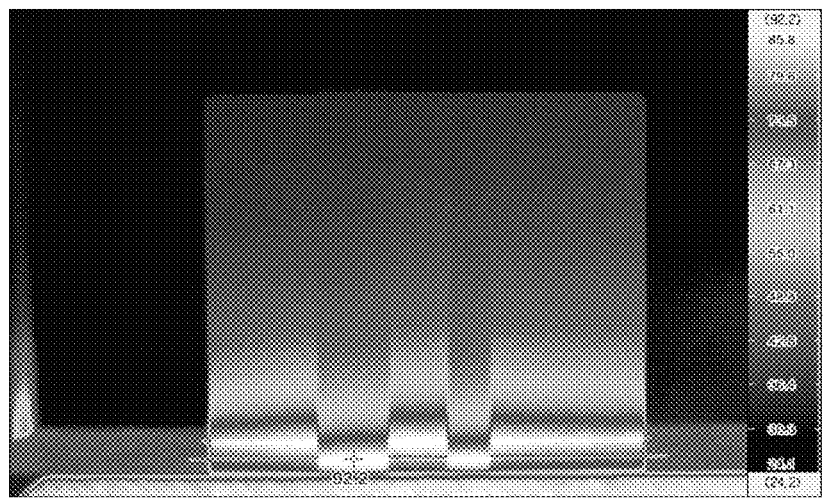
FIG. 10 is a view illustrating a thermal image of heat conduction of a solid state sample photographed in a longitudinal direction according to a conventional method.

FIG. 10 is a view illustrating a thermal image of heat conduction of a solid state sample photographed in a longitudinal direction. In the thermal image of FIG. 10, it can be seen that heat from a heat source was transferred to about one third of the sample. This means that heat radiation occurred by convection influenced by external environments. Also, it can be seen that the heat conduction could not be accurately measured in the longitudinal direction due to unstable heat supply of the heat sources (hot plate and aluminum sample support).

2. Heat Conduction Measurement Test of Present Invention

A jig for measuring heat conduction of a solid state sample, an air tempering unit, a sealed-type jig chamber for providing objective test conditions providing an environment that is not effected by external conditions. A thermal image camera was used, and the result data was created by measuring and recording heat conduction according to the lapse of time.

Cool air with a design temperature generated in the cool air unit of the air tempering unit was introduced into the jig chamber in a desired direction, and the heat radiation characteristics were measured by photographing heat radiation of the solid state sample due to convection.

a Heat Conduction Measurement in Thickness Direction

The design temperature of the air tempering unit was set to 70° C., and the surface temperature of the jig heat source 23 was increased to the design temperature. Thereafter, a sample was mounted in the jig 20 for measuring heat conduction in the thickness direction. In this case, thermal compound was thinly coated on the surface of the sample, and the sample was disposed closely to the heat source using the sample holder 24 of the jig 20 to minimize the interfacial resistance between the sample and the heat source. After the mounting of the sample, the chamber door part 11 of the jig chamber 10 was opened, and then the thermal image camera 70 was disposed at a distance of about 1 m from the sample to photograph the sample to measure data on the heat conduction (see FIG. 6).

Figure 11:
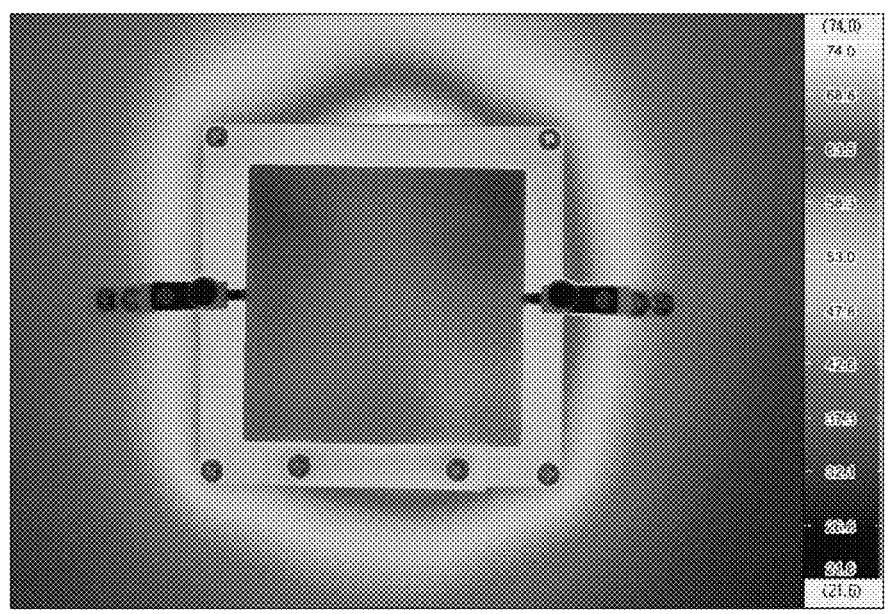
FIG. 11 is a view illustrating a thermal image of heat conduction of a solid state sample photographed in a thickness direction according to an exemplary embodiment of the present invention.

FIG. 11 is a view illustrating a thermal image of heat conduction of a solid state sample photographed in a thickness direction according to an embodiment of the present invention. In the thermal image of FIG. 11, it can be seen that the heat conduction irregularly occurred in a solid state sample. This means that the heat conduction occurred according to the characteristics of the sample. Also, the design temperature of the air tempering unit and the surface temperature of the heat source coincided with each other, and the error range of temperature according to the surface location of the heat source was about ±1° C., showing heat was very stably supplied. Accordingly, it can be seen that the heat conduction could be exactly measured in the thickness direction of the sample.

b. Heat Conduction Measurement in Radial Direction

The test and measurement of the heat conduction in the radial direction was performed similarly to the heat conduction measurement in the thickness direction except that a sample was heated using a circular plate type of heat source with a diameter of about 30 mm. When the sample was mounted in the jig for measuring heat conduction in the radial direction, thermal compound was thinly coated on the surface of the heat source instead of the sample. Since the heat source was in surface contact with one surface of the sample, in order to secure the heat source so as to accurately contact the central portion of the sample, the sample was secured using a sample to prevent the sample from moving or bending.

Although not shown, it can be seen from the thermal image that heat was conducted in the radial direction of the sample. The edge portion of the sample most distant from the heat source was measured to be at a temperature lower than about 70° C. that is a design temperature. This means that heat radiation occurred due to air convection in the jig chamber. Accordingly, it can be seen that the heat conduction according to the heat radiation in the radial direction of the sample could be accurately measured.

c. Heat Conduction Measurement in Longitudinal Direction

Since a sample had to be mounted in the jig before the jig for measuring heat conduction in the longitudinal direction is mounted in the jig chamber, the sample thinly coated with thermal compound on one end portion (about 30 mm) thereof was inserted into a pocket type heat source of the jig. In this case, when hot air cannot be smoothly transferred to the heat source due to the structure of the jig, the heat source itself may be heated for a sufficient time to reduce a difference between a design temperature and the actual temperature.

Although not shown, it can be seen from the thermal image that heat was conducted up to the end portion (portion protruding out of the jig) of the sample unlike the heat conduction measurement by a conventional method and the heat conduction time was also shortened compared to that of the conventional method. Since other portions of the jig except a portion of the heat source receiving the sample were formed of a heat-insulating material, heat inside the jig was prevented from radiating, and the measurement of the thermal image camera was for the most part free of interferences. Thus, the heat conduction in the longitudinal direction of the sample can be accurately measured by utilizing the illustrative embodiment of the present invention.

From the above tests, when the heat conduction is measured by a conventional method, thermal diffusion was observed only by a heat transfer path of the heat source (hot plate) regardless of material variables such as filler orientation and dispersion in an injection-molded composite sample and filler type. Also, since the measurement was performed in an unsealed environment, the measurement was significantly influenced by ambient convection, and the direction of the thermal diffusion was more significantly influenced by the form of the heat source than by the characteristics of the sample. Also, since the mounting location of the sample was not fixed, the mounting location of the sample was changed whenever the sample was mounted onto the heat source, and thus the reliability of the thermal diffusion imaging result was reduced. Thus, it can be seen that the heat conduction of the composite sample cannot be objectively and exactly measured.

Also, in the conventional method, since the heat radiation by cool air could not be visualized and analyzed due to an influence of ambient convection, the result data of the heat conduction measurement test was inversely calculated to derive the heat radiation characteristics of the sample.

On the other hand, in the heat conduction measurement according to the embodiment of the present invention, the thermal diffusion non-uniformly occurred in the sample according to the form of the heat source and the temperature distribution of the surface, and the heat conduction was more influenced by the characteristics of the sample than the from of the heat source. Also, the design temperature of the air tempering unit and the surface temperature of the heat source coincided with each other, and the error range of temperature according to the surface location of the heat source was significantly small, showing heat was very stably supplied. Accordingly, it can be seen that the heat conduction of the sample can be accurately measured compared to a conventional method. Also, in case of the heat conduction measurement according to the illustrative embodiment of the present invention, it was possible to visualize and analyze the heat radiation by cool air.

According to an analysis system and method for visualizing heat conduction, since it is possible to visualize and analyze thermal diffusion in the thickness direction, longitudinal direction and radial direction of a solid state sample, the heat conduction characteristics of the solid state sample can be qualitatively and accurately analyzed. Accordingly, the analysis system and method can be used to correct the heat conduction measurement method and thus standardize the heat conduction characteristics analysis. The analysis system and method can contribute reliable results data by eliminating factors affecting tests of solid state samples.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. An analysis system for visualizing heat conduction, comprising:
    a sealed jig chamber including a chamber door configured to open and close the jig chamber;
    a jig removeably mounted in the jig chamber and including a heat source in surface contact with a solid state sample to induce the heat conduction of the solid state sample;
    an air tempering unit configured to supply hot air into the jig and supply cool air into the jig chamber; and
    a thermal image camera configured to photograph the heat conduction of the solid state sample to acquire a thermal image or video,
    wherein the jig comprises at least one of a jig configured to measure the heat conduction in a thickness direction of the solid state sample, a jig configured to measure the heat conduction in a longitudinal direction of the solid state sample, and a jig configured to measure the heat conduction in a radial direction of the solid state sample, and
    wherein the jig configured to measure the heat conduction in the thickness direction includes a planar heat source that is disposed on one surface of the jig and is in contact with one entire surface of the solid state sample, and a hot air inlet and a hot air outlet configured to receive and discharge hot air for increasing a temperature of the heat source.

2. The analysis system of claim 1, wherein the jig configured to measure the heat conduction in the longitudinal direction includes a circular heat source that is disposed on one surface of the jig and is in surface contact with a center of one surface of the solid state sample, and a hot air inlet and a hot air outlet f configured to receive and discharge hot air for increasing a temperature of the heat source.

3. The analysis system of claim 1, wherein the jig configured to measure the heat conduction in the radial direction comprises a pocket type heat source that is in contact with an end portion of solid state sample, and a hot air inlet and a hot air outlet that are disposed at the opposite side of the heat source and receive and discharge hot air for increasing a temperature of the heat source.

4. The analysis system of claim 1, wherein the air tempering unit includes a hot air unit configured to generate and supply hot air for uniformly increasing a temperature of the heat source of the jig, a cool air unit configured to generate and supply cool air that flows into the jig chamber to cool the solid state sample, and a control unit configured to control a temperature of the hot air and the cool air in the air tempering unit.

5. The analysis system of claim 1, wherein the air tempering unit is connected to hot air ducts that connect a hot air outlet and a hot air inlet of the air tempering unit to a hot air inlet and a hot air outlet of the jig, respectively, and is connected to a cool air duct that connects a cool air outlet of the air tempering unit to a cool air inlet of the jig chamber.

6. The analysis system of claim 1, wherein everything except the heat source in the jig is formed of a heat-insulating material and the heat source is formed of an aluminum material.

7. An analysis method for visualizing heat conduction, comprising:
    preparing a sealed jig chamber connected to an air tempering unit configured to generate and supply hot air and cool air through a duct;
    selecting and installing a jig appropriate for heat conduction measurement of a solid state sample in the jig chamber;

inducing the heat conduction by heating a heat source of the jig using the air tempering unit and transferring heat to the solid state sample mounted in the jig through the heat source;

photographing the solid state sample using a thermal image camera to acquire a thermal image or a thermal diffusion video; and analyzing heat conduction characteristics of the solid state sample using the thermal image or the thermal diffusion video, wherein the inducing of the heat conduction comprises at least one of:

inducing the heat conduction in a thickness direction of a planar sample by allowing one surface of the planar sample to be entirely in surface contact with a planar type heat source;

inducing the heat conduction in a longitudinal direction of the planar sample by inserting only one end portion of the planar sample into a pocket type heat source to be in surface contact with the heat source while being surrounded by the heat source; and inducing the heat conduction in a radial direction by disposing the planar sample to be in surface contact with a circular heat source at a center of one surface thereof.

8. The analysis method of claim 7, comprising:

cooling the solid state sample mounted in the jig through convection by supplying cool air into the jig chamber via the air tempering unit;

photographing the solid state sample via the thermal image camera to acquire a thermal image or a thermal diffusion video according to cooling of the solid state sample; and analyzing heat conduction characteristics according to heat radiation of the sample using the thermal image or the thermal diffusion video.

9. The analysis method of claim 7, wherein the jig comprises a hot air inlet and a hot air outlet configured to receive and discharge hot air for increasing a temperature of the heat source, and everything in the jig is formed of a heat-insulating material except the heat source, wherein the heat source is formed of an aluminum material.

10. The analysis method of claim 7, further comprising minimizing a gap between the solid state sample and the heat source by coating thermal compound on a surface of the heat source after cleaning the surface of the heat source of the jig.

* * * * *